United States Patent
Safonov et al.

(10) Patent No.: US 12,017,030 B2
(45) Date of Patent: Jun. 25, 2024

(54) HYDROGEN-ENHANCED TRANSDERMAL SYSTEM

(71) Applicant: H2 Universe, LLC, Granbury, TX (US)

(72) Inventors: Marina Yu. Safonov, Granbury, TX (US); Christian S. Yorgure, Rochester, NY (US); Vladimir L. Safonov, Granbury, TX (US)

(73) Assignee: H2 Universe, LLC, Granbury, TX (US)

( * ) Notice: Subject to any disclaimer, the term of this patent is extended or adjusted under 35 U.S.C. 154(b) by 657 days.

(21) Appl. No.: 16/864,938

(22) Filed: May 1, 2020

(65) Prior Publication Data
US 2020/0345992 A1 Nov. 5, 2020

Related U.S. Application Data

(60) Provisional application No. 62/920,487, filed on May 2, 2019.

(51) Int. Cl.
| | | |
|---|---|---|
| *A61M 37/00* | (2006.01) | |
| *A61K 9/00* | (2006.01) | |
| *A61K 9/70* | (2006.01) | |
| *A61K 47/02* | (2006.01) | |
| *A61M 35/00* | (2006.01) | |

(52) U.S. Cl.
CPC ........... *A61M 37/00* (2013.01); *A61K 9/0014* (2013.01); *A61K 9/7084* (2013.01); *A61K 47/02* (2013.01); *A61M 35/10* (2019.05); *A61M 2037/0007* (2013.01)

(58) Field of Classification Search
CPC .... A61K 33/00; A61K 9/7007; A61K 9/0014; A61K 9/7084
See application file for complete search history.

(56) References Cited

U.S. PATENT DOCUMENTS

| | | | |
|---|---|---|---|
| 6,352,715 B1 | 3/2002 | Hwang et al. | |
| 8,449,908 B2 | 5/2013 | Stinchcomb et al. | |
| 9,238,012 B2 | 1/2016 | Hiraoka et al. | |
| 9,962,340 B2 | 5/2018 | Weimann | |
| 10,016,486 B1 | 7/2018 | Pyun et al. | |
| 10,071,090 B2 | 9/2018 | Stinchcomb et al. | |
| 10,272,125 B2 | 4/2019 | Weimann | |
| 2009/0326447 A1* | 12/2009 | Joshi | A61K 31/00 604/82 |
| 2018/0289629 A1* | 10/2018 | Nasrollahzadeh Abyazani | A61K 31/545 |
| 2019/0308001 A1* | 10/2019 | Safonov | C01B 3/501 |
| 2020/0030372 A1 | 1/2020 | Safonov et al. | |
| 2020/0281866 A1* | 9/2020 | Tsaur | A61K 8/0212 |

FOREIGN PATENT DOCUMENTS

| | | | | |
|---|---|---|---|---|
| DE | 10351859 A1 * | 6/2005 | ........... | A61K 8/0208 |

OTHER PUBLICATIONS

Boury et al (Green Chemistry, 2015, vol. 7, pp. 72-88) (Year: 2015).*
Kanehira (Journal of Asian Ceramic Societies, 2013, vol. 1, pp. 296-303) (Year: 2013).*
DE-10351859-A1 (Google Translation, downloaded Jul. 2023) (Year: 2023).*
Alexander, et al., "Approaches for breaking the barriers of drug permeation through transdermal drug delivery," Journal of Controlled Release, vol. 164, pp. 26-40, 2012.
Alkilani, et al., "Transdermal Drug Delivery: Innovative Pharmaceutical Developments Based on Disruption of the Barrier Properties of the stratum corneum," Pharmaceutics, vol. 7, pp. 438-470, 2015.
Dixon, et al., "The evolution of molecular hydrogen: a noteworthy potential therapy with clinical significance," Medical Gas Research, vol. 3, No. 10, 12 pages, 2013.
Herman, et al., "Essential oils and their constituents as skin penetration enhancer for transdermal drug delivery: a review," Journal of Pharmacy and Pharmacology, vol. 67, pp. 473-485, 2014.
Huang, et al., "Recent advances in hydrogen research as a therapeutic medical gas," Free Radical Research, 44(9): Sep. 2010, DD. 971-982.
Kobayashi, et al., "Hydrogen generation by reaction of Si nanopowder with neutral water," J Nanopart Res, vol. 19, 9 pages, 2017.
Nicolson, et al., "Clinical Effects of Hydrogen Administration: From Animal and Human Diseases to Exercise Medicine," International Journal of Medicine, vol. 7, pp. 32-76, 2016.
Ohta, "Recent Progress Toward Hydrogen Medicine: Potential of Molecular Hydrogen for Preventive and Therapeutic ADDlications," Current Pharmaceutical Design, 17, 2011, DD. 2241-2252.
Pastore, et al., "Transdermal patches: history, development and pharmacology," British Journal of Pharmacology, vol. 172, pp. 2179-2209, 2015.
Pereira, et al., "Traditional Therapies for Skin Wound Healing," Advances in Wound Care, vol. 5. No. 5, pp. 208-229, 2016.
Safonov, et al., "Hydrogen nanobubbles in a water solution of dietary supplement," Colloids and Surfaces A: Physicochemistry Engineering Aspects, vol. 436 (2013), DD. 333-336.

(Continued)

*Primary Examiner* — Mark V Stevens
(74) *Attorney, Agent, or Firm* — Morgan, Lewis & Bockius LLP

(57) ABSTRACT

A hydrogen-enhanced drug delivery system for hydrogen-assisted transdermal delivery of a therapeutic agent is provided. The system includes a hydrogen-generating compartment comprising at least one dry chemical. Addition of an activator, such as a liquid composition, from within or outside of the system, causes the dry chemical(s) to generate molecular hydrogen ($H_2$) within the system. The molecular hydrogen passes through a skin-contacting surface of the system, which is permeable to hydrogen and not permeable to the dry chemical(s) and the liquid composition, and enhances the release of the therapeutic agent from the system as $H_2$ is delivered to the subject's body. The $H_2$ can also enhance the therapeutic effect of the therapeutic agent.

20 Claims, 9 Drawing Sheets

(56) References Cited

OTHER PUBLICATIONS

Tamaki, et al., "Hydrogen-Rich Water Intake Accelerates Oral Palatal Wound Healing via Activation of the Nrf2/Antioxidant Defense Pathways in a Rat Model," Oxidative Medicine and Cellular Longevity, vol. 2016, 13 page, 2016.

Shields, et al., "Still too hot: Examination of water temperature and water heater characteristics 24 years after manufacturers adopt voluntary temperature setting," J Burn Care Res., vol. 34, No. 2, pp. 281-287, 2013.

* cited by examiner

HYDROGEN-ENHANCED TRANSDERMAL SYSTEM

RELATED APPLICATIONS

This application claims priority to and benefit of U.S. Provisional Application No. 62/920,487 filed May 2, 2019, the entire content of which is incorporated herein by reference.

TECHNICAL FIELD

The present disclosure relates to a hydrogen-enhanced transdermal system for administration to subject's skin for delivery of a therapeutic agent and molecular hydrogen to the subject, to provide therapeutic effects.

BACKGROUND

Hydrogen therapy includes the use of molecular hydrogen ($H_2$) for treatment and prevention of various conditions and diseases. Basic and clinical research has revealed that hydrogen is an important physiological regulatory factor with antioxidant, anti-inflammatory and anti-apoptotic protective effects on cells and organs. See Huang et al., *Recent advances in hydrogen research as a therapeutic medical gas.* Free Radical Res. (2010) 44(9): 971-82; Ohta, *Recent progress toward hydrogen medicine: potential of molecular hydrogen for preventive and therapeutic applications.* Curr Pharm Des. (2011) 17(22): 2241-52; Nicolson et al., *Clinical Effects of Hydrogen Administration: From Animal and Human Diseases to Exercise Medicine.* International Journal of Clinical Medicine. (2016) 7:32-76. Effects of the $H_2$ treatment were documented for oxidative stress-related diseases, and hydrogen-based therapy is a rapidly growing area.

Existing methods for delivering of hydrogen to a patient's body include administration of $H_2$ inhalations, oral administration of hydrogen-infused liquids (e.g., $H_2$-enriched water) or hydrogen-releasing solids (e.g., capsules or tablets), injecting $H_2$-containing solutions (e.g., $H_2$-infused saline, delivered intravenously), bathing in hydrogen-enriched water, and other ways of delivering hydrogen to the subject's body. These methods have their advantages and disadvantages and serve certain purposes of prevention, healing, and therapy.

Medical effects of drug delivery through the skin are used for treating or preventing many diseases and conditions and are widespread. However, transdermal drug delivery has its challenges, including inconsistent drug release, slow drug release, and potential side effects including toxicity.

SUMMARY OF THE INVENTION

In accordance with the present invention, this is provided a hydrogen-enhanced system comprising a therapeutic agent and a reservoir having components configured to generate molecular hydrogen ($H_2$) that diffuses to a target surface of a subject's body for a certain period of time and facilitates delivery of the therapeutic agent to the subject's body, provide additional therapeutic effect and prevent side effects of the therapeutic agent. In some embodiments, the subject is a human subject. In some embodiments, the present invention provides a hydrogen-generating system (e.g., patch, pad, bag, pouch, applicator, etc.) comprising a closed reservoir for external use on the skin for transdermal drug delivery, for an enhanced therapeutic effect that is safe, easy to use, can be self-administered, and is disposable. Accordingly, in various aspects, systems, devices, and methods for hydrogen-enhanced intradermal drug delivery to a subject (e.g., a human subject) are provided.

In some embodiments, a hydrogen-enhanced system for transdermal delivery of therapeutic agents is provided that comprises a body a body configured to be applied externally to a subject's skin, the body comprising: a first portion comprising at least one dry chemical; and a second portion comprising a therapeutic agent. A liquid activator received by the first portion causes the at least one dry chemical to generate molecular hydrogen such that the generated molecular hydrogen is released from the system and facilitates delivery of the therapeutic agent through the subject's skin. A skin-facing surface of the first portion is at least partially hydrogen-permeable and is not permeable to the dry chemical and the liquid activator. The therapeutic agent can be in the form of a solid powder or in any other form. In some embodiments, the therapeutic agent can be infused on the skin-contacting surface of the hydrogen-enhanced system, and hydrogen enhances the delivery of the therapeutic agent.

The hydrogen-enhanced system can have various configurations. For example, the system can be in the form of a transdermal patch, bag, pouch, dressing (e.g., wound dressing), bandage, etc. configured to release a therapeutic agent when applied to the skin, with assistance of $H_2$ generate when the system is activated. The system can be activated before or after the system is applied to the skin, or at the time when the system is positioned on a target area of a subject's skin.

In some embodiments, the second portion is separate from the first portion and is configured to be positioned adjacent to the subject's skin.

In some embodiments, the second portion is a skin-contacting surface of the system having the therapeutic agent disposed thereon. In some embodiments, the skin-contacting surface has an adhesive which can be deposited thereon in various ways. The adhesive can be mixed with a therapeutic agent.

In some embodiments, the at least one dry chemical of the first portion is in contact with the therapeutic agent of the second portion.

In some embodiments, the system has a third portion configured to receive the liquid activator. The system can be configured such that the liquid activator is added to the system.

In some embodiments, the system can have a third portion that releasably stores the liquid activator. The third portion can be configured to change its configuration to thereby release the liquid activator. For example, the third portion can be configured to change its configuration upon pressure applied thereto. In other implementations, the third portion can be configured to release the liquid activator in other ways. In some embodiments, the third portion storing the liquid activator can additionally store a therapeutic agent.

In some embodiments, the system has an opening that receives the liquid activator therethrough such that the liquid activator is delivered to an interior of the system and comes in contact with the at least one dry chemical to thereby cause the at least one dry chemical to generate the molecular hydrogen.

In some aspects, a method of delivering a therapeutic agent to a target area of a subject's skin is provided that comprises applying a hydrogen-enhanced drug delivery system to the target area of the subject's skin by positioning a skin-contacting surface of the system onto the target area, the system having enclosed therein a first portion comprising at least one dry chemical and a second portion comprising the therapeutic agent. The method further comprises causing a liquid composition to at least partially contact the at least one dry chemical such that the at least one dry chemical interacts with the liquid composition to cause generation of molecular hydrogen that is released from the system and facilitates penetration of the therapeutic agent through the subject's skin. In some embodiments, both hydrogen and therapeutic agent provide a therapeutic effect. Moreover, a combined therapeutic effect of the hydrogen and the therapeutic agent can be greater than the therapeutic effect of the therapeutic agent if administered alone.

In some embodiments, the second portion is a skin-contacting surface of the body. In some embodiments, the skin-contacting surface of the body has an adhesive mixed with the therapeutic agent.

In some embodiments, the method further comprises delivering the liquid composition to the system via an opening in the system.

In some embodiments, the system includes a third portion releasably storing the liquid composition. The method can comprise causing the liquid composition to be released from the third portion, and the released liquid composition at least partially contacts the at least one dry chemical such that the at least one dry chemical interacts with the liquid composition to cause generation of the molecular hydrogen. In embodiments, the liquid composition is caused to be released by applying pressure onto the third portion.

In some embodiments, the liquid composition is caused to at least partially contact the at least one dry chemical before the system is applied to the target area of the subject's skin. In some embodiments, the liquid composition is caused to at least partially contact the at least one dry chemical after the system is applied to the target area of the subject's skin.

The method in accordance with embodiments of the present disclosure can be used to treat a disease, disorder, or condition of the integumentary system in the subject in need thereof. The subject can have a disease, disorder, or condition of the integumentary system.

BRIEF DESCRIPTION OF THE DRAWINGS

Non-limiting embodiments of the present invention will be described by way of example with reference to the accompanying figures, which are schematic and are not intended to be drawn to scale. The drawings illustrate exemplary embodiments of the invention and do not therefore limit its scope. In the figures, each identical or nearly identical component illustrated is typically represented by a single numeral. For purposes of clarity, not every component is labeled in every figure, nor is every component of each embodiment of the present disclosure shown where illustration is not necessary to allow those of ordinary skill in the art to understand the present disclosure. In the figures.

DETAILED DESCRIPTION

Figure 1:
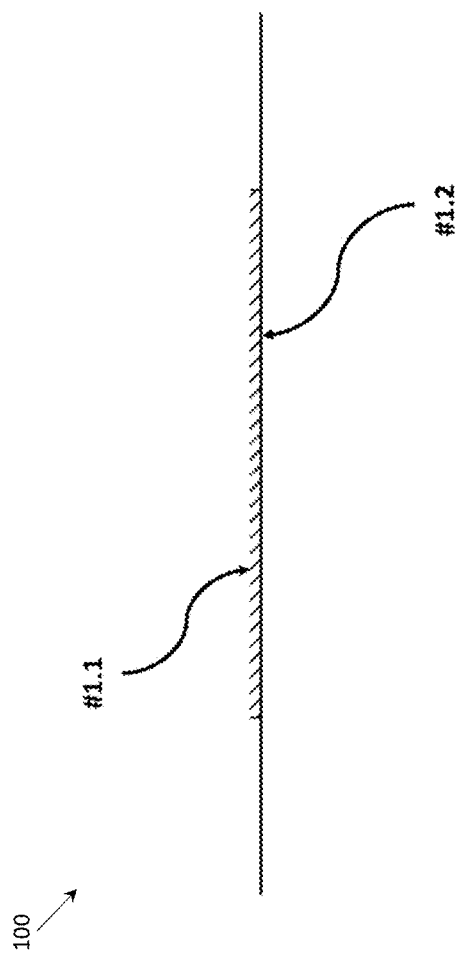
FIG. 1 is a schematic view of a hydrogen-enhanced system in accordance with embodiments of the present disclosure.

The present disclosure provides a hydrogen-enhanced, drug-releasing transdermal system comprising a therapeutic composition (e.g., one or more drugs) and components capable of generating molecular hydrogen ($H_2$) that facilitates transdermal delivery of the therapeutic composition. The present disclosure also provides techniques for manufacturing the hydrogen-enhanced transdermal system comprising a therapeutic composition that is delivered transdermally with assistance of molecular hydrogen.

Existing methods for delivering of molecular hydrogen to a patient's body include administration of $H_2$ inhalations, oral administration of hydrogen-infused liquids (e.g., $H_2$-enriched water, $H_2$-infused saline, etc.) or hydrogen-releasing solids (e.g., capsules or tablets), injecting $H_2$-containing solutions (e.g., intravenous injections), $H_2$-enriched baths, and other ways of delivering hydrogen to the subject's body. These methods have their advantages and disadvantages and serve for certain purposes of healing and therapy. Systems and methods that make use of the effects of molecular hydrogen on the skin are described in U.S. patent application Ser. No. 16/376,894, filed on Apr. 5, 2019, the entire disclosure of which is incorporated herein by reference in its entirety.

Transdermal delivery is non-invasive method of delivering drugs systemically by applying a drug formulation onto skin. Alkilani et al. (2015). *Pharmaceutics,* 7(4), 438-470. In transdermal delivery, the drug initially penetrates through the stratum corneum and then passes through the deeper epidermis and dermis. Id. The becomes available for systemic absorption via the dermal microcirculation after the drug reaches the dermal layer. Id. The stratum corneum is a barrier against drug permeability that limits therapeutic bioavailability of a bioactive. Alexander et al. (2012). *J Control Release.* 164(1):26-40. Various techniques exist for transdermal drug delivery, including iontophoresis, sonophoresis, ultrasound, electroporation, microneedles, magnetophoresis, photomechanical waves, thermal approaches (e.g., laser and radio-frequency heating), velocity-based devices (e.g., jet injectors), etc.

Topical administration of medication (e.g., via patches) can be effective and is becoming increasingly popular in treatment and prevention of many diseases and conditions. See, e.g., Pastore et al. (2015). *British Journal of Pharmacology,* 172: 2179-2209. The human skin is the outer covering of the body and is the largest organ of the integumentary system. Human skin is composed of three primary layers of tissue: the epidermis, dermis and hypodermis; and the skin has up to seven layers of ectodermal tissue and guards the underlying muscles, bones, ligaments and internal organs.

Epidermis is the outermost layer of the skin that covers almost the entire body surface and is made up of stratified squamous epithelium with an underlying basal lamina. The epidermis contains no blood vessels and it is a natural barrier to infection. The main type of cells that make up the epidermis are keratinocytes (almost 90% of the epidermis), melanocytes, Merkel cells, and Langerhans cells. The epidermis can be further subdivided into the following strata (beginning with the outermost layer): stratum corneum, stratum lucidum (only in palms of hands and bottoms of feet), stratum granulosum, stratum spinosum, and stratum basale (also called "stratum germinativum").

The dermis is the layer of skin beneath the epidermis. The dermis is made up of connective tissue along with nervous tissue, blood, and blood vessels, and the dermis cushions the body from stress and strain. The dermis is tightly connected to the epidermis by a basement membrane. The dermis is structurally divided into two areas: a superficial area adjacent to the epidermis, called the papillary region, and a deep thicker area known as the reticular region. The subcutaneous tissue (also called hypodermis and subcutis) lies below the dermis of the cutis. Its purpose is to attach the skin to underlying bone and muscle as well as supplying it with blood vessels and nerves.

Transdermal drug delivery requires that a drug or another agent pass through the epidermis to reach the microcirculation of the dermis. The stratum corneum is the top layer of the skin and varies in thickness from approximately ten to several hundred micrometers, depending on the region of the body. The stratum corneum includes layers of dead, flattened keratinocytes surrounded by a lipid matrix that together create a system that is difficult to penetrate. Most of the barrier functions of the epidermis are attributed to this layer. Bonté et al. (1997). *Archives of Dermatological Research*. 289 (2): 78-82

Accordingly, for successful transdermal delivery of a drug or another agent, the agent needs to pass through the stratum corneum. Furthermore, transdermal drug delivery is not without limitations, including inconsistent drug release, slow drug release (or, in some cases, the opposite—a burst release), limitations on delivered doses, and potential side effects including effects of drug toxicity. Also, for transdermal delivery to some skin areas (e.g., those of chronic wounds), a drug needs to pass through the dead tissue filled with pro-inflammatory cytokines to access the cells that are targets of the therapy, such that the drug can become deactivated before reaching the targeted growing tissue.

Accordingly, embodiments of the present disclosure provide improved systems and methods for transdermal delivery of therapeutic agents that is facilitated by molecular hydrogen that is simultaneously delivered transdermally. The therapeutic agents can be various drugs, cosmetics, and vaccines. Molecular hydrogen enhances therapeutic agent permeation through the skin, assisting the agent to penetrate through the stratum corneum. The molecular hydrogen diffusing from the system (e.g., a patch) pushes the molecules of the therapeutic agent through the epidermis layer of the skin and thereby accelerates their penetration into the dermis skin layer or other layers of the skin from where the therapeutic agent could be delivered to the target area of the human body. Hydrogen can promote the expression of healing-associated factors through activation of the Nrf2/antiinflamatory defense pathway and reduce proinflamatroy cytokines levels which prevents the deactivation of the drug. See Tamaki et. al. (2016). *Oxidative Medicine and Cellular Longevity*. vol. 2016, Article ID 5679040, which is incorporated by reference herein in its entirety. In some embodiments, a hydrogen-enhanced system in accordance with embodiments of the present disclosure can be used to deliver a therapeutic agent through epidermis, the stratum corneum, the stratum lucidum, the stratum granulosum, the stratum spinosum, the stratum germinativum, the basement membrane, the dermis, the papillary region of the dermis, the reticular region of the dermis, and/or the subcutis.

In some embodiments, a combined therapeutic effect of generated molecular hydrogen and a therapeutic agent can be greater than the therapeutic effect of the therapeutic agent if administered alone. In some embodiments, a combined therapeutic effect of generated molecular hydrogen and a therapeutic agent can be greater than the therapeutic effect of one or both the therapeutic agent and the molecular hydrogen if administered alone. Combined effects of therapeutic agents and molecular hydrogen, in various applications, can help in the treatment of pain, arthritis, inflammation, intoxication, wounds, ulcers, Parkinson's disease, Alzheimer's disease and in many other cases. For example, U.S. Pat. Nos. 10,272,125, 9,962,340, and 8,449,908 suggest a cannabidiol and related components transdermal delivery using a reservoir-patch design. The range of cannabidiol applications is very wide, including for treatment and prevention of pain, inflammation, intoxication, and other conditions and diseases. Cannabidiol has also been used for treatment of patients with neurological conditions, including Parkinson's and Alzheimer's diseases. It has been demonstrated in human pilot studies that molecular hydrogen helps to cure the above-mentioned diseases and conditions. In addition, molecular hydrogen may help to avoid liver damage by cannabidiol and related substances overdose.

Pain treatment using transdermal patch was disclosed, for example, in U.S. Pat. No. 10,166,199 with the formulation comprising ropivacaine or an opioid; U.S. Pat. No. 10,071,090 with the oxymorphone; and, in U.S. Pat. No. 10,016,486, with a combination of adenosine monophosphate protein kinase (AMPK) activators. In addition, U.S. Pat. No. 9,238,012 describes a transdermal patch that includes a rivastigmine-containing layer, and U.S. Pat. No. 6,352,715 describes a transdermal delivery of Huperzine A for treatment of Alzheimer's disease.

Embodiments of the present disclosure provide methods and systems that make use of generation and release of molecular hydrogen that assists in transdermal delivery of the above and other drugs. Molecular hydrogen thus provides a safe, non-invasive way of transdermal drug delivery, and the combined drug/$H_2$ effect can significantly increase the efficiency of a therapeutic agent being delivered. Non-limiting examples of therapeutic agents that can be delivered transdermally using the techniques in accordance with the present disclosure include antibacterial agents; anti-inflammatory agents; anesthetic agents (e.g., ropivacaine); antidepressants; anti-nausea medications (e.g., scopolamine); estrogen; testosterone; contraceptive medications; blood pressure medications (e.g., clonidine); opioids (e.g., fentanyl, oxymorphone, buprenorphine, etc.); medications used to treat attention deficit disorder (ADD), attention deficit hyperactivity disorder (ADHD), and narcolepsy; adenosine monophosphate protein kinase (AMPK) activators; cognition-enhancing medications (e.g., rivastigmine and other cholinesterase inhibitors); cannabidiol and cannabidiol-based agents; nitroglycerine, and others agents, including combinations of the above.

In some embodiments, therapeutic agents can be natural healing agents such as, e.g., herbs and herbal-derived compounds, oils including essential oils, and other substances. Examples of natural healing agents include *Aloe vera*,

*Hippophae rhamnoides* (sea buckthorn), *Angelica sinensis, Catharanthus roseus* (*Vinca rosea*), *Calendula officinalis* (marigold), *Sesamum indicum, Morinda citrifolia* (noni), *Camellia sinensis, Rosmarinus officinalis L.* (rosemary), primarosa oil, tea tree oil, propolis, honey or honey-containing agents, etc. See, e.g., Pereira & Bártolo. *Adv Wound Care* (New Rochelle). 2016; 5(5):208-229.

In some embodiments, the natural agents such as, e.g., essential oils, along with $H_2$, enhance penetration of different drugs from a transdermal patch into the lower skin layers. See Herman & Herman. *Journal of Pharmacy and Pharmacology,* 2015; vol. 67(4):473-485.

The therapeutic agents delivered transdermally can be used for treatments and prevention of various conditions and diseases of integumentary and other systems, including wounds, cuts, and various skin conditions and diseases. In some embodiments, the therapeutic agents can be delivered with the $H_2$ assistance for treatment of neurological conditions, psychological conditions, and various other conditions. Some diseases or conditions are not easily prevented or treated using injections, and embodiments of the present disclosure allow for an improved technique for safe delivery of various pharmaceutical compositions.

In some embodiments, the present hydrogen-enhanced systems may be used in the treatment, control, or prevention of a disease, disorder and/or condition and/or may alter, modify or change the appearance of a member of the integumentary system of a subject suffering from a disease, disorder and/or condition such as, but not limited to, acne vulgaris, acne aestivalis, acne conglobata, acne cosmetic, acne fulminans, acne keloidalis nuchae, acne mechanica, acne medicamentosa, acne miliaris necrotica, acne necrotica, acne rosacea, actinic keratosis, acne vulgaris, acne aestivalis, acne conglobata, acne cosmetic, acne fulminans, acne keloidalis nuchae, acne mechanica, acne medicamentosa, acne miliaris necrotica, acne necrotica, acne rosacea, acute urticaria, allergic contact dermatitis, alopecia areata, angioedema, athlete's foot, atopic dermatitis, autoeczematization, baby acne, balding, bastomycosis, blackheads, birthmarks and other skin pigmentation problems, boils, bruises, bug bites and stings, burns, cellulitis, chiggers, chloracne, cholinergic or stress uricara, chronic urticaria, cold type urticara, confluent and reticulated papillomatosis, corns, cysts, dandruff, dermatitis herpetiformis, dermatographism, dyshidrotic eczema, diaper rash, dry skin, dyshidrosis, ectodermal dysplasia such as, hyprohidrotic ectodermal dysplasia and X-linked hyphidrotic ectodermal dysplasia, eczema, epidermaodysplasia verruciformis, erythema nodosum, excoriated acne, exercise-induced anaphylasis folliculitis, excess skin oil, folliculitis, freckles, frostbite, fungal nails, hair density, hair growth rate, halogen acne, hair loss, heat rash, hematoma, herpes simplex infections (e.g. non-genital), hidradenitis suppurativa, hives, hyperhidrosis, hyperpigmentation, hypohidrotic ectodermal dysplasia, hypopigmentation, impetigo, ingrown hair, heat type urticara, ingrown toenail, infantile acne or neonatal acne, itch, irritant contact dermatitis, jock itch, keloid, keratosis pilaris, lichen planus, lichen sclerosus, lupus miliaris disseminatus faciei, melasma, moles, molluscum contagiosum, nail growth rate, nail health, neurodermatitis, nummular eczema, occupational acne, oil acne, onychomycosis, physical urticara, pilonidal cyst, pityriasis rosea, pityriasis versicolor, poison ivy, pomade acne, pseudofolliculitis barbae or acne keloidalis nuchae, psoriasis, psoriatic arthritis, pressure or delayed pressure urticara, puncture wounds such as cuts and scrapes, rash, rare or water type urticara, rhinoplasty, ringworm, rosacea, rothmund-thomson syndrome, sagging of the skin, scabis, scars, seborrhea, seborrheic dermatitis, shingles, skin cancer, skin tag, solar type urticara, spider bite, stretch marks, sunburn, tar acne, tropical acne, thinning of skin, thrush, tinea versicolor, transient acantholytic dermatosis, tycoon's cap or acne necrotica miliaris, uneven skin tone, varicose veins, venous eczema, vibratory angioedema, vitiligo, warts, Weber-Christian disease, wrinkles, x-linked hypohidrotic ectodermal dysplasia, xerotic eczema, yeast infection and general signs of aging.

In some embodiments, there are provided methods of treating, controlling or preventing dry skin by administering therapeutic agents using the present hydrogen-enhanced systems.

In some embodiments, there are provided methods of treating, controlling or preventing any one of the various types of psoriasis (e.g. plague psoriasis, guttate psoriasis, pustular psoriasis, inverse psoriasis, and erythrodermic psoriasis).

Various embodiments relate to the treatment, control, or prevention of eczema (e.g. atopic dermatitis, nummular eczema, dyshidrotic eczema, seborrheic dermatitis, irritant contact dermatitis, allergic contact dermatitis, dyshidrosis, venous eczema, dermatitis herpetiformis, neurodermatitis, autoeczematization and xerotic eczema).

Hives, or urticaria, including, but not limited to, acute urticaria, chronic urticara and angioedema, physical urticara, pressure or delayed pressure urticara, cholinergic or stress uricara, cold type urticara, heat type urticara, solar type urticara, rare or water type urticara, vibratory angioedema, exercise-induced anaphylasis and dermatographism may be treated using the present hydrogen-enhanced systems.

Various embodiments relate to the treatment, control, or prevention of rosacea, which includes, but is not limited to, erthematotelangiectatic rosacea, papulopustular rosacea, phymatous rosacea, and ocular rosacea.

In some embodiments, there is provided methods of treating, controlling or preventing acne using the present hydrogen-enhanced systems. For example, acne may include, but is not limited to, acneiform eruptions, acne aestivalis, acne conglobata, acne cosmetic, acne fulminans, acne keloidalis nuchae, acne mechanica, acne medicamentosa, acne miliaris necrotica, acne necrotica, acne rosacea, baby acne, blackheads, chloracne, excoriated acne, halogen acne, infantile acne or neonatal acne, lupus miliaris disseminatus faciei, occupational acne, oil acne, pomade acne, tar acne, tropical acne, tycoon's cap or acne necrotica miliaris, pseudofolliculitis barbae or acne keloidalis nuchae, and hidradenitis suppurativa.

In further embodiments, vitiligo is treated using the present hydrogen-enhanced systems. In some embodiments, the present hydrogen-enhanced systems find use in the treatment, control, or prevention of hyprohidrotic ectodermal dysplasia (HED). In some embodiments, the present hydrogen-enhanced systems find use in the treatment, control, or prevention of balding, or hair thinning (e.g. male pattern baldness, or androgenetic alopecia (AGA)).

The present hydrogen-enhanced systems can also find use in methods of treatment, control, or prevention of scars and stretch marks (striae).

Epidermodysplasia verruciformis (also known as Lutz-Lewandowsky epidermodysplasia), a rare autosomal recessive genetic hereditary skin disorder, may also be treated using the hydrogen-enhanced systems of the present invention, e.g. by targeting transmembrane channel-like 6 (EVER1) or transmembrane channellike 8 (EVER2) genes.

In some embodiments, skin sagging, thinning or wrinkling may be treated, controlled or prevented using the present hydrogen-enhanced systems, e.g. by delivering therapeutic agents that target one or more proteins such as collagen, elastin, fibroblast growth factor 7, TIMP metallopeptidase inhibitors, matrix metallopeptidases, superoxide dismutase and other extracellular matrix proteins and proteoglycans.

In some embodiments, hydrogen-enhanced systems in accordance with the present disclosure may be used for wound treatment. In some embodiments, methods of treating, controlling or preventing wounds using the using the present hydrogen-enhanced systems comprises additional steps of, for example, cleaning the wound bed to facilitate wound healing and closure, including, but not limited to: debridement, sharp debridement (surgical removal of dead or infected tissue from a wound), optionally including chemical debriding agents, such as enzymes, to remove necrotic tissue; wound dressings to provide the wound with a moist, warm environment and to promote tissue repair and healing (e.g., wound dressings comprising hydrogels (e.g., AQUASORB; DUODERM), hydrocolloids (e.g., AQUACEL; COMFEEL), foams (e.g., LYOFOAM; SPYROSORB), and alginates (e.g., ALGISITE; CURASORB); administration of growth factors to stimulate cell division and proliferation and to promote wound healing e.g. becaplermin; and (iv) soft-tissue wound coverage, a skin graft may be necessary to obtain coverage of clean, non-healing wounds (e.g., autologous skin grafts, cadaveric skin graft, bioengineered skin substitutes (e.g., APLIGRAF; DERMAGRAFT)).

In various embodiments, a hydrogen-enhanced system in accordance with embodiments of the present disclosure can be used for skin healing after a variety of cosmetic/plastic surgery procedures, including, without limitation, a surgical procedure involving skin grafting and an aesthetic or cosmetic surgery (e.g. a facial plastic surgery procedure including, but not limited to blepharoplasty, rhinoplasty, rhytidectomy, genioplasty, facial implants, otoplasty, hair implantation, cleft lip and cleft palate repair, and/or a body plastic surgery procedure including but not limited to abdominoplasty, brachioplasty, thigh lift, breast reduction, breast augmentation, body contouring, liposuction, hand surgery).

In some embodiments, skin cancer is treated using a hydrogen-enhanced system in accordance with embodiments of the present disclosure. For instance, the skin cancer is one or more of actinic keratosis, basal cell carcinoma, melanoma, Kaposi's sarcoma, and squamous cell carcinoma. The present hydrogen-enhanced systems can also find use in the treatment of various stages of cancers, including skin cancers (e.g. basal cell cancer (BCC), squamous cell cancer (SCC), and melanoma), such as a stage of the American Joint Committee on Cancer (AJCC) TNM system (e.g. one or more of TX, T0, Tis, T1, T1a, T1b, T2, T2A, T2B, T3, T3a, T3b, T4, T4a, T4b, NX, N0, N1, N2, N3, M0, M1a, M1b, M1c) and/or a staging system (e.g. Stage 0, Stage IA, Stage IB, Stage IIA, Stage IIB, Stage IIC, Stage IIIA, Stage IIIB, Stage IIIC, Stage IV).

Furthermore, in some embodiments, the hydrogen-enhanced systems in accordance with the present disclosure can be used to deliver to a subject (e.g., a human patient) drugs or other therapeutic agents that are not well suitable for delivery via injections. Also, some conditions or diseases may not be amenable for treatment via injectable drugs, and the present hydrogen-assisted transdermal systems may allow treatment or prevention of such conditions or diseases.

The advantage of the systems and methods in accordance with embodiments of the present disclosure is to obtain molecular hydrogen in a closed reservoir by a chemical reaction or in other ways, using an activator. In the described systems, all substances are in a closed reservoir, have no direct contact with the skin and therefore cannot cause any skin irritation or other undesirable side effects. Only molecular hydrogen gas arising during activation of the system (e.g., a patch) diffuses through a skin-contacting layer and penetrates the skin thereby enhancing a transdermal delivery of a therapeutic agent releasably carried by the system. The described hydrogen-enhanced systems are self-contained, easy to use, transport and store, and can be self-administered.

In embodiments, a hydrogen generating patch comprises of a closed reservoir or container in which a mixture of chemicals or substance(s) with hydrogen storage is in a dry state. In the dry mixture, no reactions occur, and no hydrogen is generated. In this form, the device is safe for transportation and storage. This system is supplemented by the method of delivering an aqueous solution of other chemical for mixing with dry chemicals and activating a chemical reaction in which molecular hydrogen is generated.

In some embodiments, a hydrogen-enhanced transdermal system (e.g., a patch, bag, or another form) is activated before use. Activation is achieved by adding an aqueous solution (e.g., an aqueous solution of suitable chemical(s)) into a hydrogen-generated system with dry reagents. Then the system is applied to the target site on the body. The chemical reaction or substance with hydrogen storage in the system produces molecular hydrogen. The molecular hydrogen gas easily diffuses through a plastic, fabric, or another material of the system and penetrates into the tissues of the body.

In some embodiments, a therapeutic agent can be infused in the transdermal patch skin layer and pushed out of this layer into the skin by hydrogen produced in the patch reaction reservoir, and released through the drug-infused skin layer pushing drug out of this layer and delivering the drug into a human body.

Dry compounds that can be included in a transdermal patch in accordance with embodiments of the present disclosure can be various biopolymers and nano-materials that can store a significant amount of hydrogen. Some of these materials release hydrogen when aqueous solutions are applied. The dry compounds can be selected based on known hydrogen-releasing chemical reactions (e.g., the reactions of the electrochemical series of elements (Ca, Mg, Al, Zn, Fe) with water, acids or bases). The dry chemicals are selected for inclusion in a hydrogen-enhanced transdermal patch based on their safety, ecological compatibility, stability to long-term storage, and other factors. Reagents should not cause burns and other unpleasant consequences for patients if a surface of the patch (e.g., plastic) is accidentally broken.

In some embodiments, the hydrogen-generating or hydrogen-storing dry compounds included in a hydrogen-enhanced drug delivery system can be mixture of chemicals included in a reservoir or coated onto substrates (not readily permeable to hydrogen) capable of generating hydrogen. The mixture is composed of dry chemicals that do not react with each other. The hydrogen reservoir system is activated by the addition of water or other chemical aqueous solution. The transdermal patch is placed on the target area of the body with a hydrogen-permeable side. The reaction that occurs inside the patch generates hydrogen for a certain period of time, and molecular diffusion forces of hydrogen cause the molecules of the drug to be transferred to the target body surface and to penetrate through the skin into the body, to provide a desired therapeutic effect.

In some embodiments, the present invention provides a hydrogen-generating patch including a closed reservoir in combination with a therapeutic agent (e.g., drug or vaccine) for external use on the skin for an enhanced therapeutic effect. Hydrogen-enhanced transdermal patches can include, in the same reservoir, both drug a therapeutic agent and hydrogen-generating components comprising dry chemicals or substances with hydrogen storage. The hydrogen-generating components can be in the form of powder (which can be homogeneous, heterogeneous, or compressed powder), pellets, layers, and other solids.

The systems and methods in accordance with the present disclosure provide for the enhancement of the action of a transdermal patch configured to deliver a therapeutic agent in combination with molecular hydrogen, for application to the skin for the targeted therapy. Compared with a hydrogen patch (that does not deliver a therapeutic agent) or a patch with a medicine, the combined patch in accordance with the present disclosure has certain advantages. In particular, $H_2$ penetrating into the skin increases the activity of the cells, gives a local boost, which naturally contributes to improved drug absorption. Conventional transdermally delivered drugs are typically formulated together with skin permeation chemical enhancers, also referred to as penetration enhancers (e.g., ethanol, propylene glycol, oleic acid, azone, terpenes and bile acids). The present hydrogen-enhanced transdermal patch does not require a drug to have added chemicals in the form of enhancers.

Further, the effect of hydrogen can reduce the side effects of the drug, due to its anti-inflammatory and immune system boosting effects. In addition, the compatible combination of a therapeutic agent and molecular hydrogen gas is safe, because $H_2$ does not react with the chemical compound—of therapeutic agent at human body temperature.

In embodiments, a hydrogen-enhanced transdermal system is self-contained, easy to use, transport and store, and can be self-administered. For example, the system can be in the form of a transdermal patch, bag, pouch, dressing, bandage, etc. configured to release a therapeutic agent when applied to the skin and modified to include a portion with components that can generate $H_2$ when the system is activated, before, during, or after it is applied to the skin. The portion can be, e.g., a reservoir where a hydrogen-generating chemical reaction is activated before application of the system to the skin. Molecular hydrogen gas diffuses easily through skin contact layer of the reservoir, and penetrates the skin, while other components of the chemical reaction, including an activator (e.g., water or other liquid, residue or an aqueous composition), remain inside the reservoir.

In some embodiments, dry chemical compounds that generate $H_2$ upon activation can be in the form of a layer formed, for example, of the dry chemicals in the form of a compressed powder.

In embodiments of the present disclosure, dry chemical compounds enclosed within a system (e.g., a sealed enclosure or closed reservoir) of the hydrogen-enhanced system and capable of generating molecular hydrogen are disposed separately from the subject's skin, such that the compounds remain separated from the skin during hydrogen release through a skin-contacting surface of the system. Thus, the system delivers hydrogen without any detrimental effects on the skin. In some embodiments, the hydrogen is generated as required, upon a certain action performed with respect to the housing and/or its features. In this way, the hydrogen is administered, along with a therapeutic agent, to a desired target area, at a desired time, and for a certain duration time that is sufficient to provide a therapeutic effect. The chemical compounds include dry compounds that can generate $H_2$ upon coming in contact with an activator (e.g., liquid), liquid compounds that are mixed only once the system is activated and can be imbedded (infused) in the patch skin layer. Before the activation, the hydrogen-delivering system can be safely transported and stored. Moreover, the hydrogen-delivering system is self-contained and it can be made suitable for self-administration, such that it can be used outside a clinical setting.

The hydrogen-enhanced system or device in accordance with the present disclosure can have various configurations. For example, the system can be a pad, patch, bag, pouch, bandage, compress, wound dressing, band, tape, mask or any other type of a transdermal applicator configured to enclose therein one or more chemical compounds capable of generating molecular hydrogen upon activation of the housing so as to enhance a therapeutic agent delivery to a subject. The chemical compounds are selected such that they react in a safe way, without generating excess of hydrogen (which may be flammable in extreme circumstances). Also, when more than one dry chemical is used, they do not react until the dry chemicals are mixed with an activator such as an aqueous composition. Non-limiting examples of the aqueous composition include a water suspension of calcium hydroxide, a water solution of sodium chloride and copper (II) sulfate, water, a suitable acid, base, and other suitable solutions. Non-limiting examples of the dry compounds include electrochemical series, e.g., aluminum, magnesium, zinc, iron; and compounds such as, e.g., magnesium hydride, calcium hydride, biopolymers and other suitable dry compounds where hydrogen is stored and is released once in contact with a liquid (e.g., water or another liquid) solution, or their mixture(s). Molecular hydrogen can be produced from a suitable chemical reaction, or it can be released from molecular storage. Components used to produce hydrogen are safe and, in some embodiments, are Generally Recognized As Safe (GRAS)-certified.

The hydrogen-enhanced, drug-releasing system in accordance with embodiments of the present disclosure can be administered for treatment of various conditions and disorders. For example, in some embodiments, the system can be administered to a subject that has a disease, disorder, or condition of the integumentary system. The system can thus be used in a method of treatment of a subject that causes a treatment and/or mitigation of the disease, disorder, or condition of the integumentary system.

The application of the hydrogen-enhanced, drug-releasing system in accordance with embodiments of the present disclosure may alter, modify and/or change the appearance of a member of the integumenary system of a subject such as, but not limited, to skin, hair and nails. Such alteration, modification and/or change may be in the context of treatment methods and/or therapeutic uses as described herein including, by way of non-limiting examples, dermatological treatments and cosmetics procedures.

A hydrogen-enhanced, drug-releasing system in accordance with embodiments of the present disclosure can have various configurations. For example, in some embodiments, the system can be in the form of a conventional transdermal patch that includes a hydrogen-generating portion. A therapeutic agent can be releasably stored in the system in various forms. For example, in some embodiments, a transdermal patch can have a single layer including both a drug and an adhesive. Thus, in this type of patch, the adhesive layer, which serves to adhere the patch to the skin, is also responsible for the release of the therapeutic agent, which occurs as $H_2$ is generated by the system and released therefrom. The adhesive layer can include a temporary liner on one side, and it can have a hydrogen-generating compartment on another side (which can be separated from the adhesive layer by an activator layer that allows for more even distribution of an activator as it comes in contact with the dry chemicals capable of generating molecular hydrogen).

Furthermore, in some embodiments, a hydrogen-enhanced, drug-releasing system can include an additional compartment (e.g., a layer) including a second therapeutic agent. For example, a first therapeutic agent, included in the adhesive layer, can be released from the system as the molecular hydrogen is generated, and the second therapeutic agent can be formulated for a more prolonged release.

As another example, in some embodiments, a hydrogen-enhanced, drug-releasing system can be a transdermal system that includes a separate therapeutic agent layer. The therapeutic agent layer can be a liquid compartment containing a drug solution or suspension separated, e.g., in the form of an encapsulated reservoir (made of, e.g., a drug-impermeable metallic plastic laminate). In such embodiments, the release of the therapeutic agent from the therapeutic agent compartment or layer can be triggered in response to a certain action, e.g., removal of a protective layer or in response to any other action (depending on the configuration of the patch). As in other embodiments, the drug release from the patch is assisted by the molecular hydrogen generated within the patch when the patch is "activated" such that a liquid activator is brought in contact with dry hydrogen-generating and/or hydrogen-storing chemicals in the patch.

FIG. 1 is a schematic illustrating a principle of a design of a hydrogen-enhanced, drug-releasing system 100 in accordance with embodiments of the present disclosure. The hydrogen-enhanced, drug-releasing system 100 can be in the form of a hydrogen-enhanced adhesive transdermal patch comprising a hydrogen generating formulation deposited on a surface of a transdermal adhesive patch. The hydrogen generating formulation can be activated by body heat, by wetting the area of application on the skin, by wetting the system 100, or in another way or a combination thereof. The activation of the hydrogen generating formulation sets off the hydrogen generation, which facilitates the drug permeability through the skin and/or enhances the effect of the drug. In the system 100, as shown schematically in FIG. 1, a mixture of the hydrogen generating formulation, an adhesive, and the (collectively labeled as "#1.1") is coated onto a substrate (#1.2) that is substantially impermeable to $H_2$. As used herein, the "substantially" means that the substrate 1.2 allows less than about 20%, or less than about 15%, or less than about 10%, or less than about 5%, or less than about 1% of $H_2$ to pass therethrough. In some embodiments, the substrate 1.2 allows less than about 10% of $H_2$ to pass therethrough. Non-limiting examples of adhesives include acrylate-based adhesives, polyisobutylene adhesive, hydrophilic polymers and copolymers, and the silicone adhesive(s) and combination thereof. The adhesives are suitable for application to skin.

Furthermore, in some embodiments, a hydrogen-enhanced, drug-releasing system comprises a hydrogen-generating formulation mixed with a drug and a binding agent (e.g., a hydrogel, molecularly imprinted polymer(s), or combinations thereof). The binding agent (e.g., an adhesive) has adhesive properties and allows the system to be releasably adhered to a target area of a subject's skin. The mixture is coated onto a substrate which is used to fabricate a ready-for-use hydrogen-enhanced transdermal patch.

The molecular hydrogen can be generated in various ways. For example, a hydrogen-enhanced, drug-releasing system can include dry components that, upon activation, enter into a chemical reaction that results in generation of $H_2$. In some embodiments, a hydrogen-enhanced, drug-releasing system can include components as described in U.S. patent application Ser. No. 16/376,894, filed on Apr. 5, 2019, the entire disclosure of which is incorporated herein by reference in its entirety.

In some embodiments, a hydrogen-enhanced, drug-releasing system in accordance with embodiments of the present disclosure can be a patch, pad, or another type of a system configured to be releasably attached to the skin. The system can include an absorbent portion that can releasably include components that can react to release $H_2$ and at least one therapeutic agent.

Figure 2:
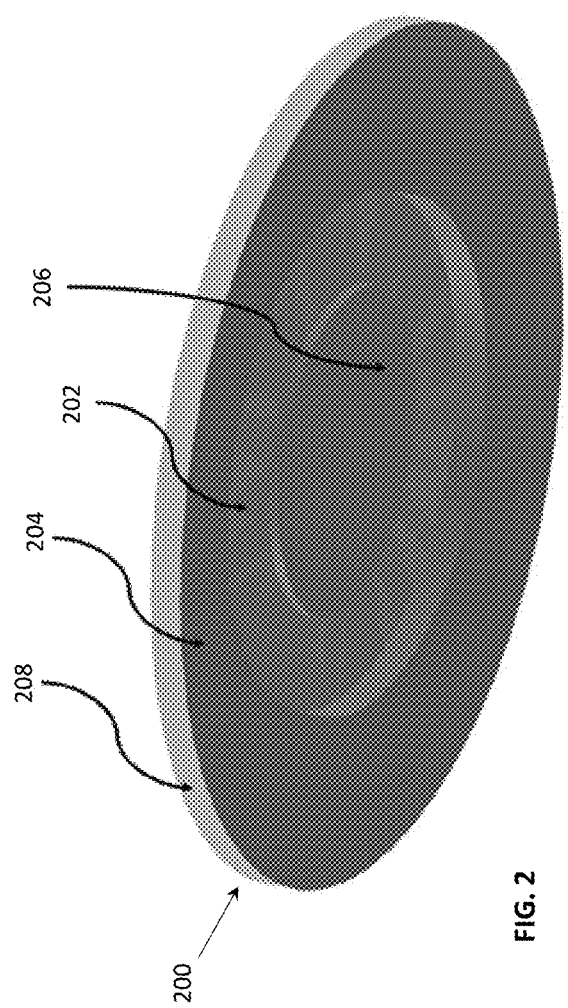
FIG. 2 is a prospective view of a hydrogen-enhanced system in accordance with some embodiments of the present disclosure.

FIG. 2 illustrates an example of a hydrogen-enhanced, drug-releasing system 200 in the form of a hydrogen-enhanced matrix/monolithic transdermal patch. The system 200 can also be in the form of a dressing, for more prolonged application. In this example, the system 200, which is generally circular, includes an absorbent substrate 202 (e.g., in the form of a pad or patch) disposed on an adhesive substrate 204 that is configured to be positioned onto the skin surface. It should be appreciated, however, that the system 200 can have any suitable shape, including oval, rectangular, square, or any other regular or irregular shape. The adhesive substrate 204 has adhesive properties that allow it to be releasably attached to the subject's skin. In this example, the adhesive substrate 204 has a larger area than the absorbent substrate 202 such that, in FIG. 2, a portion of the adhesive substrate 204 is shown concentrically around the absorbent substrate 202. It should be appreciated however that the absorbent substrate 202 can be disposed in other ways on the adhesive substrate 204.

In the example of FIG. 2, a formulation comprising hydrogen-generating components and one or more therapeutic agents (e.g., drugs), is deposited into a portion 206 (e.g., a well or recess) of the absorbent substrate 202. In this example, the absorbent substrate 202 is substantially circular in shape and it forms the substantially circular recess 206. The recess 206 can have deposited therein the hydrogen-generating components and the therapeutic agent(s). It should be appreciated, however, that the formulation can be deposited onto the absorbent substrate 202 in other manners. For example, instead of a circular recess 206, one or more recesses having other shapes can be formed. Also, the recesses can form patterns within the absorbent substrate 202. Furthermore, in some implementations, the hydrogen-generating components and the therapeutic agent(s) can be incorporated into the absorbent substrate 202 in other ways, e.g., throughout the entire body of the absorbent substrate 202 (rather than in a certain area). The system 200 can be attached to the skin. In some embodiments, like in the present example, a protective covering 208 (e.g., fabric, polymer, or another material) is disposed over the absorbent substrate 202 and the adhesive substrate 204. The protective covering 208 can be removably attached to the adhesive substrate 204, and the covering 208 is removed before the system 200 is attached to the skin.

The system 200 can be activated to generate and release $H_2$ in various ways. For example, it can be activated using body heat, sweat, added liquid (e.g., purified water or another liquid), exudates (e.g., when the system 200 is a dressing or a part of a dressing) could activate the process, producing hydrogen which aids in moving the drug through the skin (for the transdermal patch) or to the wound (for wound dressing application) more efficiently.

Figure 3A:
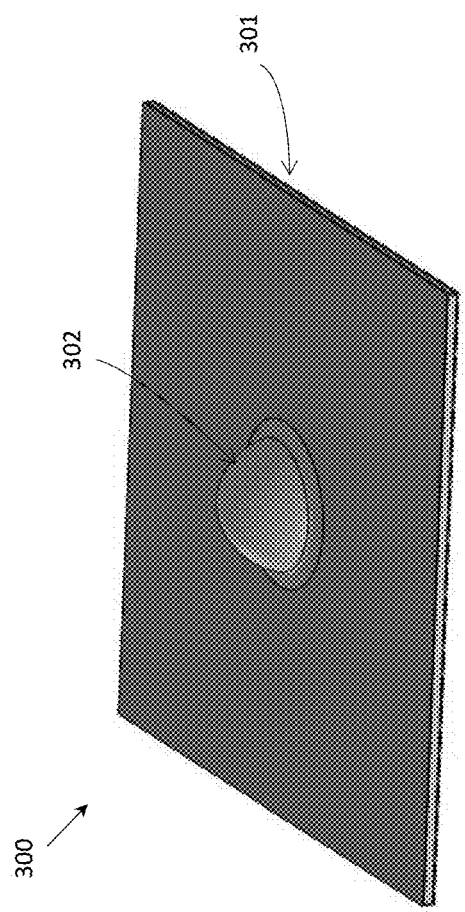
FIG. 3A is a prospective view of another hydrogen-enhanced system that is configured to be activated by applying pressure thereto, in accordance with some embodiments of the present disclosure.
Figure 3B:
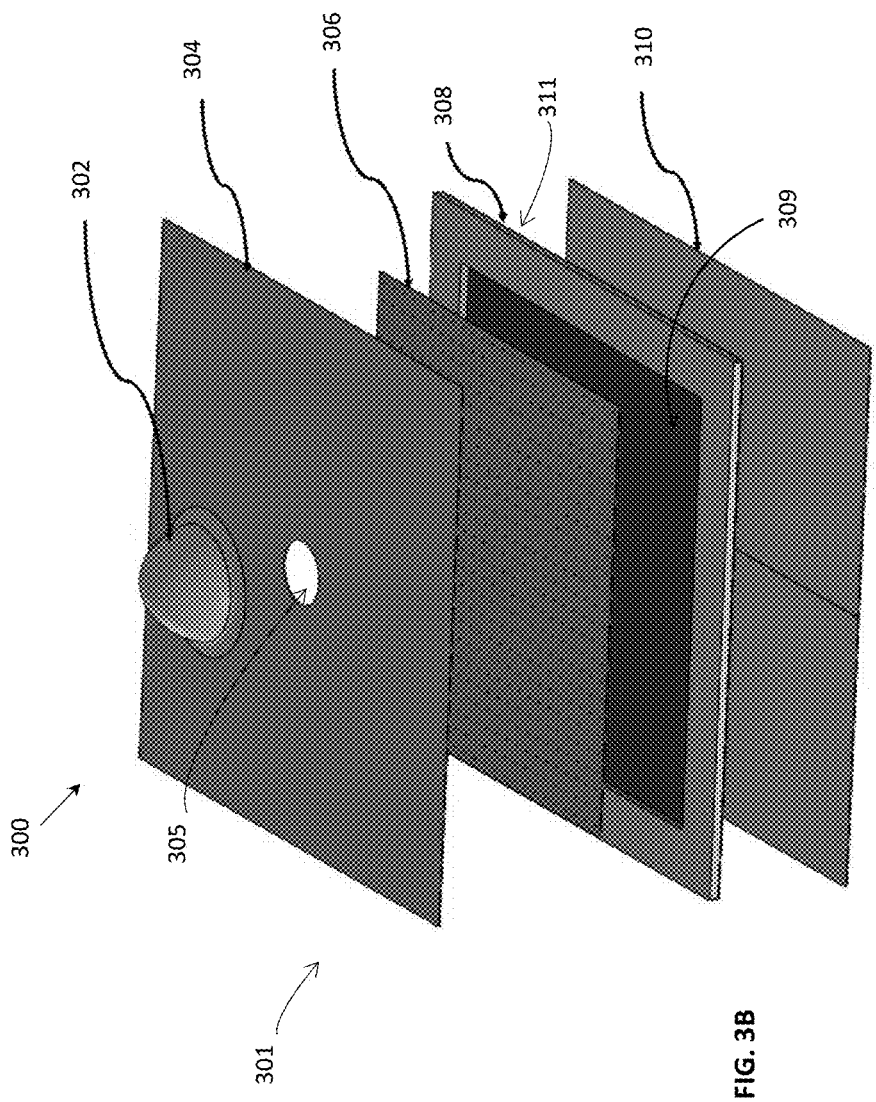
FIG. 3B is an exploded view of the hydrogen-enhanced system of FIG. 3A.
Figure 3C:
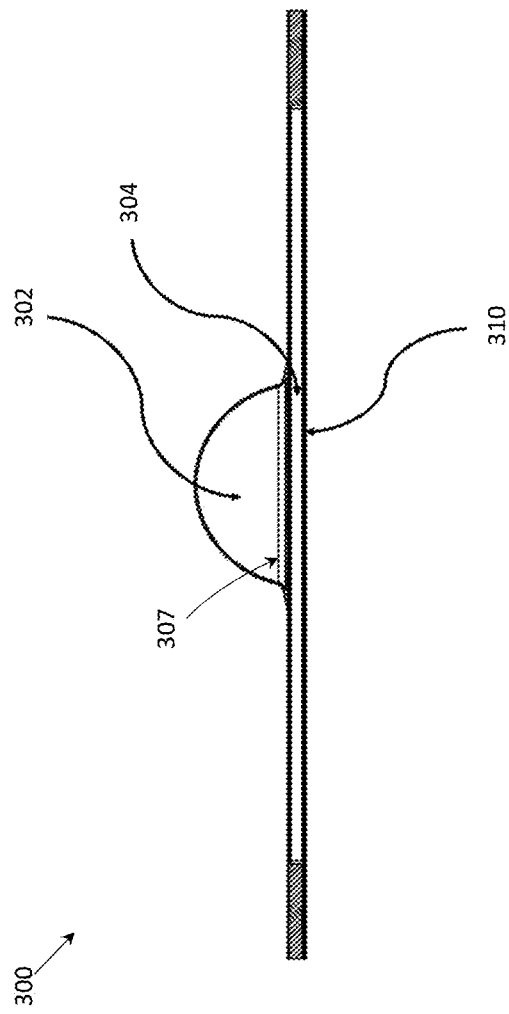
FIG. 3C is a cross-sectional review of the hydrogen-enhanced system of FIG. 3A.

FIGS. 3A, 3B, and 3C illustrate an embodiment of a hydrogen-enhanced transdermal system or patch 300 comprising a capsule or reservoir 302 (e.g., a reagent blister including an activator such as an aqueous solution) disposed on a multi-layered body 301 of the patch 300 that includes dry chemicals or substance with hydrogen storage that can be activated by the activator delivered from the closed reservoir 302. The reservoir 302 can be formed from a flexible material such that pressure can be applied to the reservoir 302 to thereby allow its content be released to the interior of the system 300. In this example, the reservoir 302 at least partially protrudes from the surface of the body 301 of the patch 300.

As shown in FIG. 3B wherein the reservoir 302 is shown displaced from its position in the assembled patch 300, the patch 300 comprises an activator layer 306 separated from the reservoir 302 by a low hydrogen-permeable layer 304 (e.g., an aluminum foil layer or another layer made of metal or another material), a hydrogen-generating compartment 308 having a skin-contacting layer 311 on its surface facing the skin (obscured in FIGS. 3A and 3B), and a protective layer 310 that protects the skin-contacting layer 311. A top surface of the low hydrogen-permeable layer 304 can be made from a backing material that allows the system 300 to be comfortably worn by a subject.

In this example, the reservoir 302 can include an activator such as an aqueous solution, and the diffusion layer 306 is configured to ensure uniform distribution of an activator (e.g., the aqueous solution releasably stored in the reservoir 302) during application of the patch 300 onto a target area of the skin. The hydrogen-generating compartment 308 includes, in its interior 309, a mixture of dry chemical compounds that can enter a chemical reaction to generate $H_2$ upon coming in contact with an activator. In some embodiments, the hydrogen-generating compartment 308 can also include biopolymers and other organic and inorganic compounds such as, e.g., xanthane gum, microcrystalline cellulose, maltodextrin, saccharine, agar-agar, sodium chloride, potassium chloride, etc., that regulate the rate of a chemical reaction that leads to generation of $H_2$.

The skin-contacting layer 311 can have at least one therapeutic agent releasably incorporated therein and an adhesive. The skin-contacting layer 311 can be made such that it is soft, flexible, and not irritating to the skin, to ensure patient's comfort during application of the system 300. For example, in some embodiments, the skin-contacting layer 311 can be made from a suitable plastic material or a combination of materials. In some embodiments, additionally or alternatively, the skin-contacting layer can be formed of a fabric material that is not permeable to water and dry hydrogen-generating chemical reagents, but that allows hydrogen to penetrate therethrough. In some embodiments, the skin-contacting layer 311 can be in the form of a membrane having at least one therapeutic agent releasably incorporated therein.

The hydrogen-enhanced system in accordance with embodiments of the present disclosure is activated for hydrogen-assisted delivery of a therapeutic agent. This involves bringing a liquid composition into contact with the dry reagents, which leads to a chemical reaction that releases molecular hydrogen. In some embodiments, one or more dry chemical compounds enclosed in the housing of the hydrogen-delivering system are hydrogen-storage compounds that release the stored hydrogen upon contact with a liquid (e.g., aqueous) composition. The hydrogen-storage compounds can be, for example, complex organic polymers that are filled with molecular hydrogen. When interacting with a solution (e.g., a water solution), hydrogen escapes from its storage. The system is applied to the target site on the subject's body before or after the system is activated to generate molecular hydrogen. The chemical reaction or substance(s) with hydrogen storage in the enclosed housing of the hydrogen-delivering system produces molecular hydrogen. The thus generated molecular hydrogen gas diffuses at least through the skin-contacting surface of the housing, and, as it penetrates through the subject's skin and underlying tissues, the molecular hydrogen assists transdermal delivery of the therapeutic agent.

Referring to FIG. 3B, the low hydrogen-permeable layer 304 has an opening 305 over which a bottom surface 307 (facing the low hydrogen-permeable layer 304, obscured in FIG. 3B and shown in FIG. 3C) of the reservoir 302 can be disposed. The bottom surface 307 of the reservoir 302 is configured to allow at least a portion of the content of the reservoir 302 to pass therethrough. For example, the bottom surface 307 can be at least partially permeable to reagents included in the reservoir 302. The bottom surface 307 can be at least at least partially removable, e.g., it can be configured such that it can break or otherwise change its configuration to allow the content of the reservoir 302 be released to the interior of the system 300. In some embodiments, the reservoir 302 can include at least one therapeutic agent, in addition to the activator. In other embodiments, however, the at least one therapeutic agent can be incorporated into the skin-contacting layer 311.

In use, the patch 300 can be activated when pressure is applied onto the activator reservoir (or reagent reservoir) 302, in the direction towards the low hydrogen-permeable layer 304. As a result, at least a portion of the contents of the activator reservoir 302 is released from the activator reservoir 302 and is passed onto the diffusion layer 306 where the content mixes with the chemical compounds in the hydrogen-generating compartment 308. The diffusion layer 306, which can be in the form of a highly absorptive, semi-hydrophilic membrane or thermally bond combination of viscose and polypropylene substrates, facilitates spreading of the content of the reservoir 302 over the surface of the hydrogen-generating compartment 308 such that more even contact of the aqueous solution with the dry chemical compounds in the hydrogen-generating compartment 308 occurs. The dry chemical compounds can be incorporated into the hydrogen-generating compartment 308 is various ways. For example, the dry chemical compounds can be in the form of a pressed powder or in another form that allows them to reside in the hydrogen-generating compartment 308.

A skin-facing surface of the skin-contacting layer 311 has at least a portion thereof that is permeable to $H_2$ but not permeable to the dry chemicals included in the hydrogen-generating compartment 308 and is not permeable to an activator (e.g., water or another liquid) and to product(s) of the chemical reaction between the hydrogen-generating or hydrogen-storing chemicals included in the hydrogen-generating compartment 308.

Once at least a portion of the content of the activator reservoir 302 comes in contact with the chemical compounds of the hydrogen-generating compartment 308, $H_2$ can be generated by the chemical compounds. The molecular diffusion force of generated $H_2$ aids in moving the therapeutic agent (e.g., a drug) from the skin-contacting layer 311, which is at least partially permeable to $H_2$, such that the therapeutic agent, assisted by the molecular hydrogen, is administered to the skin and passed through the skin. Furthermore, in some embodiments, the therapeutic agent can additionally or alternatively be stored in the reservoir 302, and the generation of $H_2$ facilitates the transfer of the therapeutic agent towards the skin-contacting surface 311, and the generated $H_2$ enhances penetration of the therapeutic agent through the skin. Furthermore, in embodiments in which the transdermal system is configured to deliver more than one drug, the activator reservoir 302 can be a reservoir including a second drug of a drug-combination patch.

The patch 300 can be activated (e.g., by applying force onto the reservoir 302) after the patch 300 has been disposed over a target area of the skin such that the skin-contacting layer 311, with the protective layer 310 disposed over it, is positioned onto the skin area to be treated. In some embodiments, the patch 300 can be activated before it is attached to the target area of the skin. As mentioned above, the skin-contacting layer 311 can include an adhesive that allows affixing the patch 300 to the skin. The protective layer 310 (which can be made from paper, fabric, or a polymer (e.g., film) can be removable such that it is removed from the patch 300 before the patch 300 is applied to the skin.

Figure 4A:
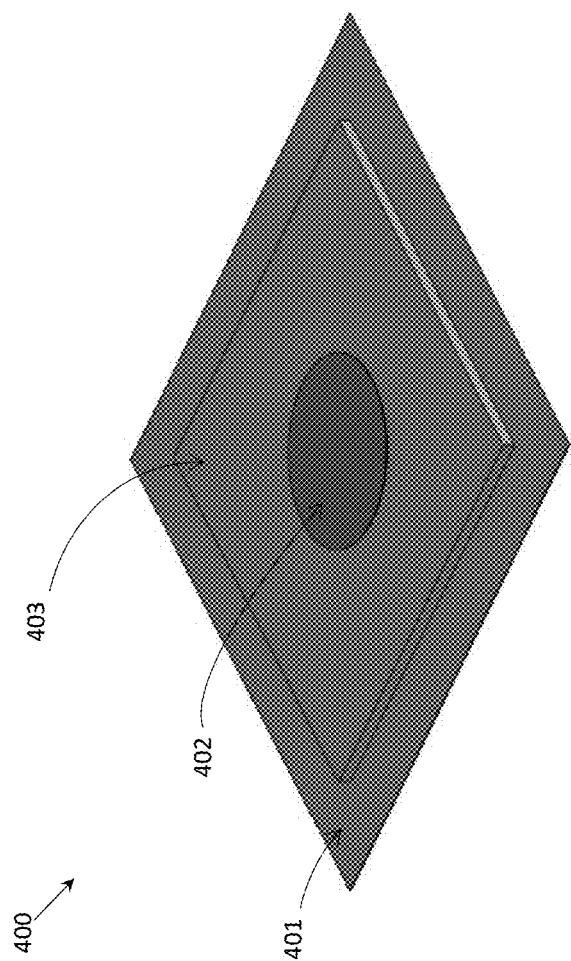
FIG. 4A is a prospective view of another hydrogen-enhanced system that is configured to be activated by delivery of an activator thereto, in accordance with some embodiments of the present disclosure.
Figure 4B:
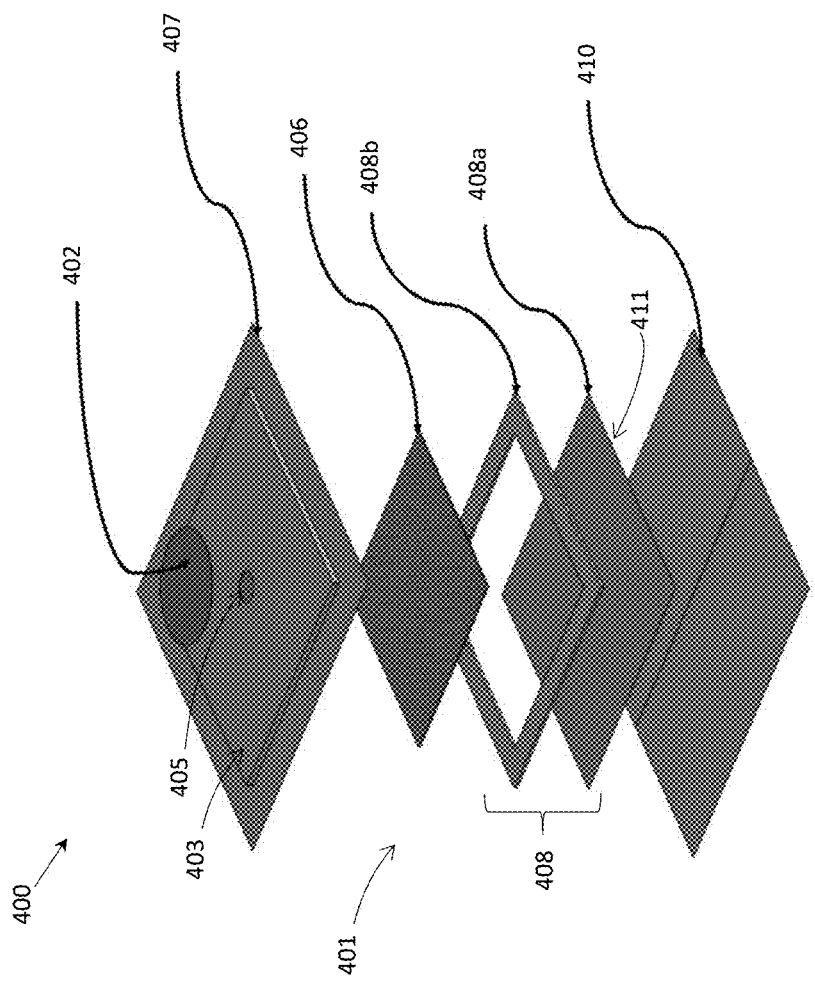
FIG. 4B is an exploded view of the hydrogen-enhanced system of FIG. 4A.

FIGS. 4A and 4B illustrate an embodiment of an example of a hydrogen-enhanced system 400 in accordance with the present disclosure. The system 400 can be in the form of a wound dressing that is a combination transdermal drug delivery system in accordance with embodiments of the present disclosure.

FIG. 4A, in which the system 400 is shown in the assembled configuration, illustrates that the system 400 comprises a body 401, a top cover portion 403 disposed on the body 401 and having a raised profile relative to the top cover portion 403, and a cover 402 positioned on the top cover portion 403. As shown in FIG. 4A, where the system 400 is shown in an exploded view, the top cover portion 403 has an opening 405 through which an activator (e.g., water or another liquid) can be delivered to the system 400. For example, the activator can be delivered from a separate container (e.g., a "drop-tainer" or another form of a container) that can be part of a kit including the system 400.

The opening 405 becomes accessible when the cover 402, which is positioned in the assembled system 400 as shown in FIG. 4A, is displaced so as to expose the opening 405 and is then returned to its original position after the activator is transferred to within the system 400. In other implementations, the system 400 is manufactured such that the cover 402 is used to seal the opening only after the activator is delivered to the system 400 via the opening 405. An activator can be delivered to the system 400 through the opening 405 and can enter the top cover portion 403. It should be appreciated that the specific location of the opening 405 (i.e., the central location in the top cover portion 403) is shown in FIG. 4B by way of example only, as the opening 405 can be disposed in other places in the system 400.

As shown in FIG. 4B, the body 401 of the system 400 comprises a top surface 407, a diffusion component or layer 406, a hydrogen-generating compartment 408 having a skin-contacting layer 411 on its surface facing the skin (obscured in FIGS. 4A and 4B), and a protective layer 410 that protects the skin-contacting layer 411. When the activator is delivered to the system 400, the activator flows onto the diffusion layer 406, mixing with chemical compounds in the hydrogen-generating compartment 408, which can be a reaction reservoir or chamber. In this example, as shown in FIG. 4B, the hydrogen-generating compartment 408 includes an inner portion 408a including hydrogen-generating compound(s) and an outer portion 408b in the form of a frame configured to be positioned around the inner portion 408a. The diffusion layer 406 can be positioned inside the hydrogen-generating compartment 408 such that the diffusion layer 406 is disposed within the outer portion 408b. Also, in some embodiments, the outer portion (e.g., a frame component) 408b can be positioned so as to reinforce and hold together several components of the body 401.

In some embodiments, the skin-contacting layer 411 can include an adhesive and a therapeutic agent. In use, when the activator is provided to the system 400 and it causes components of the hydrogen-generating compartment 408 to generate $H_2$, the molecular diffusion forces of the generated hydrogen aid in moving the therapeutic agent (disposed on the skin-contacting layer 411) through the skin in an expedited manner for a quicker result.

Furthermore, in some embodiments, the skin-contacting layer 411 may not include an adhesive and it can be coated with a non-stick layer. The non-stick coating prevents the skin-contacting layer 411 from sticking to an open wound surface and may not have adhesive. The protective layer 410, which can be disposed on the skin-contacting layer 411, can be one-piece or a split liner serving to protect the skin contact side from debris, dirt and contamination. In some embodiments, prior to use, the skin-contacting layer 411 is covered with protective layer 410, such as a removable liner, that is removed before the system 400 is placed onto a target area of the subject's skin.

In some embodiments as shown in FIG. 4B, the system 400 can include an extension (low perimeter area) of layer 407 that attach the system 400 to a surface of the subject's skin when the skin-contacting layer 411 (without the layer 410) is positioned over a target area of the subject's skin, with its skin-facing surface positioned over the target area. The attachment elements can be formed in any other manner. In the embodiments of the present disclosure, the attachment element(s) is part of 407 are formed around the entire skin-contacting layer 411, or around a portion of the skin-contacting layer 411 Also, in some implementations, the system 400, which can operate as a wound dressing, can be configured to be attached to a subject's body using a bandage, elastic band, or any other one or more attachment features which can be separate from the system 400.

A hydrogen-enhanced system in accordance with embodiments of the present disclosure can be used to deliver an effective dose of a therapeutic agent in an amount that is sufficient to treat a targeted disease or condition. An effective dose of the therapeutic agent can be selected based on a desired treatment time, area of a subject's skin, type of a targeted disease or condition, pharmacokinetic and pharmacodynamic properties of the therapeutic agent, subject's general health, and other factors. For example, the effective dose can be about 1 mg/day, about 2 mg/day, about 3 mg/day, about 4 mg/day, about 5 mg/day, about 10 mg/day, about 20 mg/day, about 30 mg/day, about 40 mg/day, or about 50 mg/day. In some embodiments, the effective dose is no more than about 10 mg/day. The system can be configured to generate from about 0.1 mg to about 10 mg, or from about 0.5 mg to about 10 mg, or from about 0.5 to about 5 mg, or from about 0.5 mg to about 3 mg, or from about 0.5 mg to about 1.5 mg, or about 1 mg of $H_2$. In some embodiments, the system can be configured to generate about 1 mg of $H_2$ that is sufficient to effectively deliver the therapeutic agent to the subject's body.

In some embodiments, a hydrogen-enhanced system in accordance with the present disclosure includes an additional component or layer having a therapeutic agent. The therapeutic agent can be in a dry, wet, moist, or a combination thereof forms. The therapeutic agent-containing layer can have a therapeutic agent releasably incorporated thereon in various ways. For example, the therapeutic agent-containing layer can be saturated or infused with a therapeutic agent. In some embodiments, the therapeutic agent-containing layer can be impregnated with a therapeutic agent (e.g., when the therapeutic agent is in the dry form).

Figure 5:
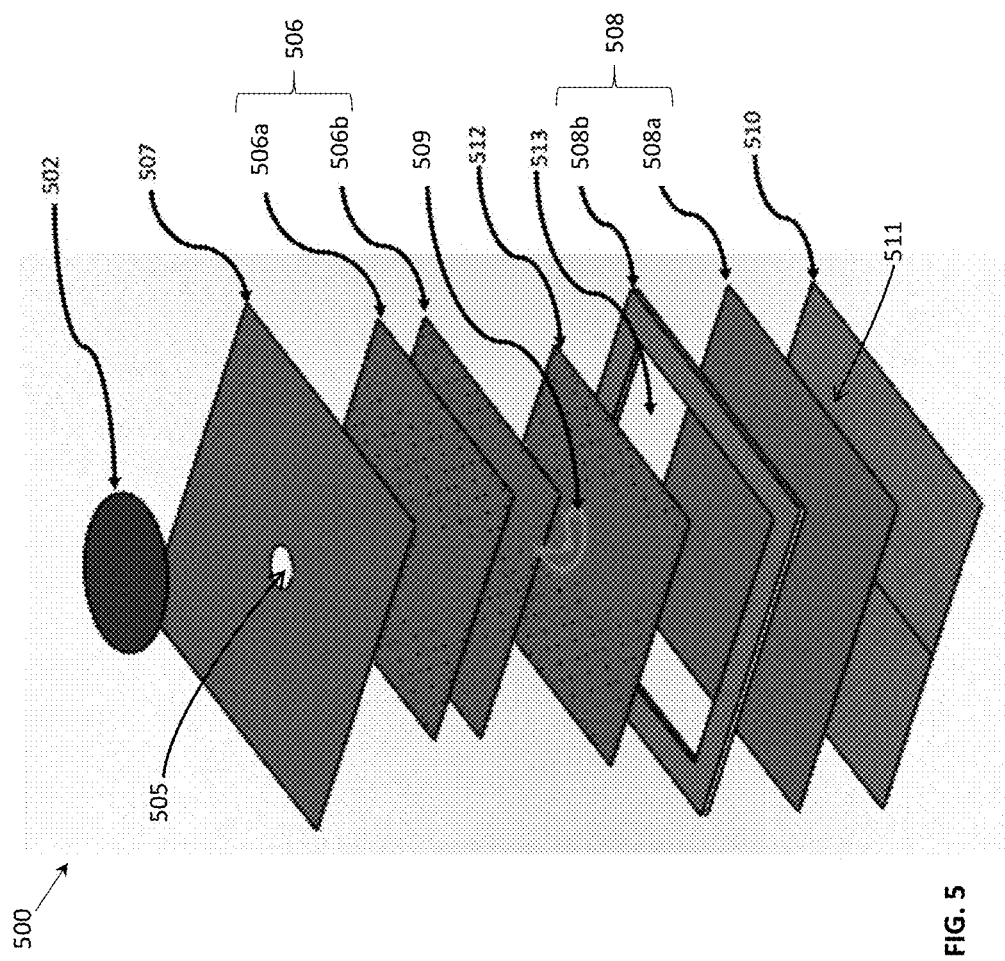
FIG. 5 is an exploded view of a hydrogen-enhanced system in accordance with some embodiments of the present disclosure.

FIG. 5 illustrates another example of a hydrogen-enhanced system 500 in accordance with embodiments of the present disclosure. The system 500 comprises a top surface or layer 507, diffusion components or layers 506a, 506b forming a diffusion system 506 (which can be a single component in some implementations), a hydrogen-generating compartment 508 comprising an inner compartment 508a including hydrogen-generating compound(s) and an outer portion 508b, a therapeutic agent-containing layer 512, and a protective layer 510. The top layer 507 (formed from a low hydrogen-permeable material) has an opening 505 through which an activator (e.g., water or another liquid) can be delivered to the system 500. As shown in FIG. 5, the opening 505 in the top layer 507 can be covered by a removable cover 502. The activator can be delivered to the system 500 from a separate container that can be, in some embodiments, part of a kit including the system 500. The two components 506a, 506b are used to facilitate the spread of the activator for improved contact with the hydrogen-generating compounds. In some embodiments, the hydrogen-generating compounds are in the form of a powder, and the soaking of the diffusion layers with the activator helps to remain the powdered hydrogen-generating compounds in place. It should be appreciated however that one diffusion component, or more than two diffusion components can be used. Also, the diffusion components can have various shapes and configurations, and they can be in the form different from layers.

As schematically shown in FIG. 5, the hydrogen-generating compartment 508 includes a reaction chamber or reservoir 513 where the hydrogen-generating chemical reaction takes place. In the assembled configuration of the system 500, the reaction chamber 513 comprises the hydrogen-generating compartment 508. Similar to other embodiments of hydrogen-enhanced systems in accordance with embodiments of the present disclosure, the hydrogen-generating compartment 508 of the system 500 has a skin-contacting layer 511 comprising adhesive material. The adhesive material can be any suitable adhesive that can be used to attach the system 500 to a subject's skin. In addition, the system 500 can have a removable protective layer 510 (e.g., medial grade paper, film liner, etc.) that protects the adhesive before the use of the system 500. As also shown schematically in FIG. 5, in the illustrated example, hydrogen-generating compounds 509 can be disposed on the therapeutic agent-containing layer 512. The hydrogen-generating compounds 509 can be in the form of a dry powder. In some embodiments, the hydrogen-generating compounds 509 can be in a liquid, gel, powder, paste, or another form.

In use, when the system 500 is activated by an addition of an activator therein (which can be received via the opening 505), the activator comes in contact with the diffusion system 506 having the diffusion layers 506a, 506b. The diffusion system 506 absorbs the activator that diffuses through the diffusion layers 506a, 506b and comes in contact with the hydrogen-generating compounds 509 disposed on the therapeutic agent-containing layer 512. The diffusion system 506 facilitates the more even spread of the activator around the hydrogen-generating compounds 509 disposed in the reaction chamber 513. The hydrogen-generating reaction occurs when the activator reaches the hydrogen-generating compounds 509 in the reaction chamber 513. The outer portion 508b of the hydrogen-generating compartment 508 forms the walls of the reaction chamber 513, similar to outer portion 408b of system 400 (FIG. 4B).

In the hydrogen-enhanced system of FIG. 5, a therapeutic agent is included in or forms a separate layer that can overlay a compartment including hydrogen-generating compounds. In some embodiments, a therapeutic agent can be stored (e.g., as a powder) in the same compartment that includes hydrogen-generating compounds. In some embodiments, the therapeutic agent can be disposed (e.g., infused) on a skin-contacting surface of the system. Also, in some embodiments, a liquid therapeutic agent can be added into the system and it can be used as an activator that activates a hydrogen-generating reaction. The liquid therapeutic agent can also be added in addition to the activator. Furthermore, in some embodiments, an example of which is shown in FIGS. 3A and 3B, a therapeutic agent can be releasably stored along with an activator (e.g., in reservoir 302 of FIGS. 3A and 3B).

Figure 6:
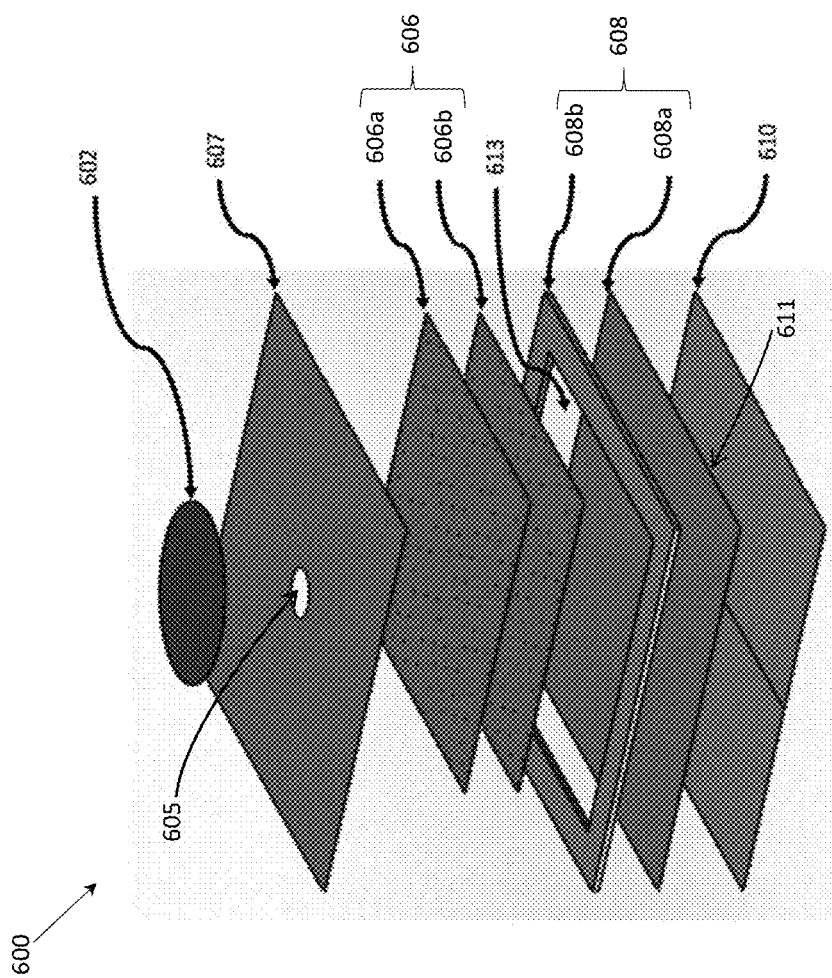
FIG. 6 is an exploded view of another hydrogen-enhanced system in accordance with some embodiments of the present disclosure.

FIG. 6 illustrates an example of a hydrogen-enhanced system 600 (e.g., a transdermal patch) in accordance with embodiments of the present disclosure. The system can include a therapeutic agent on its skin-contacting surface or stored along with hydrogen-generating compounds, or a therapeutic agent can be added to the system when the system is in use.

As shown in FIG. 6, the system 600 comprises a top surface or layer 607, diffusion layers 606a, 606b forming a diffusion system 606 (which can be a single component in some implementations), a hydrogen-generating compartment 608, comprising an inner compartment 608a including hydrogen-generating compound(s), and an outer portion 608b, and a protective layer 610. The top layer 607 (formed from a low hydrogen-permeable material) has an opening 605 through which an activator (e.g., water or another liquid) can be delivered to the system 600. As shown in FIG. 6, the opening 605 in the top layer 607 can be covered by a removable cover 602. The activator can be delivered to the system 600 from a separate container that can be, in some embodiments, part of a kit including the system 600.

As schematically shown in FIG. 6, the hydrogen-generating compartment 608 includes a reaction chamber or reservoir 613 where the hydrogen-generating chemical reaction takes place. In the assembled configuration of the system 600, the reaction chamber 613 comprises the hydrogen-generating compartment 608. The outer portion 608b of the hydrogen-generating compartment 608 forms the walls of the reaction chamber 613. Similar to other embodiments of hydrogen-enhanced systems in accordance with embodiments of the present disclosure, the hydrogen-generating compartment 608 of the system 600 has a skin-contacting layer 611 comprising adhesive material. The adhesive material can be any suitable adhesive that can be used to attach the system 600 to a subject's skin. In addition, the system 600 can have the removable protective layer 610 (e.g., paper, film liner, etc.) that protects the adhesive before the use of the system 600. The system 600 can include one or more therapeutic agents that is releasably deposited on the skin-contacting layer 611. The therapeutic agent(s) can be mixed with the adhesive. In some embodiments, however, the therapeutic agent(s) and the adhesive can be in the form of separate layers or portions.

In the example of FIG. 6, hydrogen-generating compounds are disposed in the reaction chamber 613 that comprises the hydrogen-generating compartment 608. The hydrogen-generating compounds can be in the form of a dry powder. In some embodiments, the hydrogen-generating compounds can be in a liquid, gel, powder, paste, or another form. In some embodiments, the one or more therapeutic agents can be also disposed in the reaction chamber 613. The therapeutic agent (e.g., in the form of a powder or another form) can be intermixed with the hydrogen-generating compounds, or the therapeutic agent can be separated from the hydrogen-generating compounds by a barrier which can be a dissolvable barrier or another barrier that allows the therapeutic agent to be released from the system 600 when the system is applied to a subject's skin.

Also, as another option, in some embodiments, one or more therapeutic agents to be delivered from the system 600 may not be included in the system 600 during manufacturing. Rather, the therapeutic agent can be added to the interior of the system 600 when the system 600 is positioned on a target area of a subject's body. For example, the therapeutic agent can be provided to the system 600 via the opening 605 in the top surface of the system, in which case the therapeutic agent can be mixed with an activator that activates the hydrogen-generating compounds or the therapeutic agent can be delivered to the system 600 separately from the delivery of the activator. Also, in some implementations, the therapeutic agent can be delivered to the system via a separate opening, or in another matter.

In use, when the system 600 is activated by an addition of an activator therein (which can be received via the opening 605), the activator comes in contact with the diffusion system 606 having the diffusion layers 606a, 606b. The diffusion system 606 absorbs the activator that diffuses through the diffusion layers 606a, 606b and comes in contact with the hydrogen-generating compounds of the hydrogen-generating compartment 608. The diffusion system 606 facilitates the more even spread of the activator around the hydrogen-generating compounds, and the hydrogen-generating reaction occurs when the activator reaches the hydrogen-generating compounds.

In various embodiments, an efficiency of a permeation of a therapeutic agent through the skin can be improved due to assistance from molecular hydrogen generated and released from a hydrogen-enhanced system. In some embodiments, the efficiency of the therapeutic agent permeation can be greater than about 30%, or greater than about 40%, or greater than about 50%, or greater than about 60%, or greater than about 70%, or greater than about 80%, or greater than about 90%, or greater than about 95%.

In some embodiments, greater than about 30%, or greater than about 40%, or greater than about 50%, or greater than about 60%, or greater than about 70%, or greater than about 80%, or greater than about 90%, or greater than about 95% of a dose of a therapeutic agent can be delivered to the systemic circulation due to assistance from molecular hydrogen.

It should be appreciated that, in some embodiments, hydrogen-enhanced systems described above, or similar systems in accordance with embodiments of the present disclosure, can be associated with additional features that assist in penetration of a therapeutic agent into the systemic circulation via skin. For example, in some embodiments, the systems can additionally include microneedles or other features that additionally assist in the agent delivery to the body. In some implementations, however, no additional features are included, and a delivery of a therapeutic agent is assisted only by the molecular hydrogen generated within the system.

In some embodiments, the released hydrogen is transferred into the target area of the skin and assists the therapeutic agent to penetrate through the skin and be absorbed into the systemic circulation as the hydrogen diffuses into the underlying tissues of the subject's body.

A hydrogen-enhanced system can be used to deliver one or more therapeutic agents in various treatment regiments. A regimen can include an application of the system once a day, more than once a day, once a week, several times a week, and other frequency of the application. The hydrogen can be delivered to the target area for a certain period of time, selected to be sufficient to provide a desired enhancement effect. The period of time can be, for example, from about 1 minute to about two hours, from about 1 minute to about one hour, from about 1 minute to about 30 minutes, from about 1 minute to about 20 minutes, from about 1 minute to about 10 minutes, from about 10 minutes to about 30 minutes. In some embodiments, the period of time can be from about 30 minutes to about 2 hours. In some embodiments, the period of time can be from about 1 hour to about 8 hours, or from about 1 hour to about 6 hours, or from about 2 hours to about 8 hours, or from about 2 hours to about 6 hours. In some embodiments, the period of time can be from about 1 hour to about 24 hours, or from about 1 hour to about 20 hours, or from about 1 hour to about 15 hours, or from about 1 hour to about 12 hours, or from about 1 hour to about 10 hours, or from about 1 hour to about 9 hours. In some embodiments, the hydrogen-enhanced system can be configured to be worn overnight. In some embodiments, the period of time can be 1 day, two days, or more than two days. The period of time can depend on a size, shape, and other properties of the hydrogen-enhanced transdermal system, type of treatment, properties of a therapeutic agent being delivered, the area being treated, subject's characters, and other factors.

The hydrogen enhanced transdermal system can be configured to release hydrogen for a predetermined duration of time. In the course of therapy, multiple hydrogen-enhanced system in accordance with embodiments of the present disclosure can be applied to a target skin area (which can be intact or wounded skin area). For example, the therapy can involve application of the same or different hydrogen-enhanced systems to the target area over a period of a day, several days, a week, several weeks or over any other period of time.

DEFINITIONS

The following definitions are used in connection with the invention disclosed herein. Unless defined otherwise, all technical and scientific terms used herein have the same meaning as commonly understood to one of skill in the art to which this invention belongs.

Further, the term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

EXAMPLES

Example 1

A hydrogen enhanced system includes a component (e.g., hydrogen-generating compartment 308 of FIG. 3B, hydrogen-generating compartment 408 of FIG. 4B, or another type of hydrogen-generating compartment) that has metallic aluminum (e.g., foil, powder, or another form) that is covered by aluminum oxide. An activator such as a water suspension of calcium hydroxide, $Ca(OH)_2$ ("slaked lime"), when in contact with the metallic aluminum covered by aluminum oxide, activates the following set of chemical reactions to generate $H_2$:

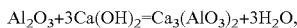

$Al_2O_3+3Ca(OH)_2=Ca_3(AlO_3)_2+3H_2O$,

$2Al+6H_2O=2Al(OH)_3+3H_2\uparrow$,

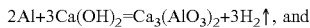

$2Al+3Ca(OH)_2=Ca_3(AlO_3)_2+3H_2\uparrow$, and

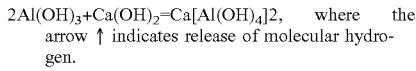

$2Al(OH)_3+Ca(OH)_2=Ca[Al(OH)_4]2$, where the arrow ↑ indicates release of molecular hydrogen.

Example 2

A hydrogen-enhanced system includes a component (e.g., hydrogen-generating compartment 308 of FIG. 3B, hydrogen-generating compartment 408 of FIG. 4B, or another type of a hydrogen-generating compartment) that includes a metallic magnesium (e.g., flakes or powder) that is covered by magnesium oxide. An activator such as a water suspension of citric acid, when in contact with the metallic magnesium covered by magnesium oxide, activates the following reaction to generate $H_2$:

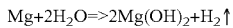

$Mg+2H_2O=>2Mg(OH)_2+H_2\uparrow$ where the arrow ↑ indicates release of molecular hydrogen.

In these examples, the reaction occurs with the release of minor short term heat and the formation of hydrogen. The release of heat can be beneficial in some cases, since the heat, in combination with the release of a therapeutic agent and molecular hydrogen, can have additional therapeutic effect. Also, heat may have a placebo effect on the subject (e.g., a human patient).

In these examples, biopolymers and other organic and inorganic compounds such as, e.g., xanthane gum, microcrystalline cellulose, maltodextrin, saccharine, agar-agar, sodium chloride, potassium chloride, etc., can be added to the reaction mixture to regulate the rate of the chemical reaction.

Molecular hydrogen generated by a hydrogen-enhanced system in accordance with some embodiments of the present disclosure can enhance transdermal delivery of various therapeutic agents, including drugs that can be used to treat various conditions.

Since other modifications and changes varied to fit particular operating requirements and environments will be apparent to those skilled in the art, the invention is not considered limited to the examples chosen for purposes of disclosure, and covers all changes and modifications which do not constitute departures from various embodiments, or combinations of the embodiments, of the invention.

In some embodiments, for improved contact with the skin, the skin surface or the skin-facing surface of the housing can be treated with a compound such as, e.g., a moisturizing cream or a disinfectant liquid. The compound is selected such that its application does not affect or prevent diffusion of hydrogen into the skin or other tissues.

Equivalents

While the present disclosure has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not patentable in view of such publications.

As used herein, all headings are simply for organization and are not intended to limit the disclosure in any manner. The content of any individual section may be equally applicable to all sections.

What is claimed is:

1. A method of delivering a therapeutic agent to a target area of a subject's skin, the method comprising:
   applying a hydrogen-enhanced drug delivery system to the target area of the subject's skin by positioning a body comprising a skin-contacting surface of the system onto the target area, the body of the hydrogen-enhanced drug delivery system having enclosed therein:
   1) a first portion comprising an aluminum powder, $Ca(OH)_2$, and one or more biopolymers;
   2) a second portion comprising the therapeutic agent; and
   3) a third portion configured to releasably store a liquid activator or to receive a liquid activator through an opening,
   wherein the skin-contacting surface is at least partially hydrogen-permeable and is not permeable to the aluminum powder, Ca(OH)$_2$, one or more biopolymers, and the liquid activator; and causing the liquid activator to at least partially contact the aluminum powder, Ca(OH)$_2$, and the one or more biopolymers such that the aluminum powder, Ca(OH)$_2$, and the one or more biopolymers interacts with the liquid activator to cause generation of molecular hydrogen that is released from the system through the skin-contacting surface thereby facilitating penetration of the therapeutic agent through the subject's skin.

2. The method of claim 1, wherein the second portion is a skin-contacting surface of the body of the hydrogen-enhanced drug delivery system.

3. The method of claim 2, wherein the skin-contacting surface of the body of the hydrogen-enhanced drug delivery system has an adhesive mixed with the therapeutic agent.

4. The method of claim 2, wherein the therapeutic agent is infused on the skin-contacting surface.

5. The method of claim 1, wherein the one or more biopolymers comprises xanthan gum, microcrystalline cellulose, maltodextrin, saccharine, or agar-agar.

6. The method of claim 1, wherein the third portion comprises a cover to seal the opening after delivering the liquid activator.

7. The method of claim 1, wherein the liquid activator comprises one or more of water, a water suspension of calcium hydroxide, a water solution of sodium chloride and copper (II) sulfate, and a suitable acid or base.

8. The method of claim 1, further comprising delivering the liquid activator through the opening before the hydrogen-enhanced drug delivery system is applied to the target area of the subject's skin; or wherein delivering the liquid activator is performed after the hydrogen-enhanced drug delivery system is applied to the target area of the subject's skin.

9. The method of claim 1, wherein the subject has a disease, disorder, or condition of the integumentary system, and the method causes a treatment and/or mitigation of the disease, disorder, or condition of the integumentary system.

10. A method of delivering a therapeutic agent to a target area of a subject's skin, the method comprising:

applying a hydrogen-enhanced drug delivery system to the target area of the subject's skin by positioning a body comprising a skin-contacting surface of the system onto the target area, the body of the hydrogen-enhanced drug delivery system having enclosed therein:

1) a first portion comprising an aluminum powder, Ca(OH)$_2$, microcrystalline cellulose, and xanthan gum;

2) a second portion comprising the therapeutic agent; and 2) a third portion configured to releasably store a liquid activator or to receive a liquid activator through an opening, wherein the skin-contacting surface is at least partially hydrogen-permeable and is not permeable to the aluminum powder, Ca(OH)$_2$, microcrystalline cellulose, xanthan gum, and the liquid activator; and causing the liquid activator to at least partially contact the aluminum powder, Ca(OH)$_2$, microcrystalline cellulose, and xanthan gum to cause generation of molecular hydrogen that is released from the system through the skin-contacting surface thereby facilitating penetration of the therapeutic agent through the subject's skin.

11. The method of claim 1, wherein the therapeutic agent comprises herbs, herbal-derived compounds, oils, essential oils, Aloe vera, *Hippophae rhamnoides*, sea buckthorn, *Angelica sinensis, Catharanthus roseus, Vinca rosea, Calendula officinalis*, marigold, *Sesamum indicum, Morinda citrifolia*, noni, *Camellia sinensis, Rosmarinus officinalis L.*, rosemary, primrose oil, tea tree oil, propolis, honey, or honey-containing agents.

12. The method of claim 1, comprising causing the liquid activator to be to be released from the third portion by applying pressure onto the third portion.

13. The method of claim 10, wherein the second portion is a skin-contacting surface of the body of the hydrogen-enhanced drug delivery system.

14. The method of claim 13, wherein the skin-contacting surface of the body of the hydrogen-enhanced drug delivery system has an adhesive mixed with the therapeutic agent.

15. The method of claim 13, wherein the therapeutic agent is infused on the skin-contacting surface.

16. The method of claim 10, wherein the third portion comprises a cover to seal the opening after delivering the liquid activator.

17. The method of claim 10, wherein the liquid activator comprises one or more of water, a water suspension of calcium hydroxide, a water solution of sodium chloride and copper (II) sulfate, and a suitable acid or base.

18. The method of claim 10, further comprising delivering the liquid activator through the opening before the hydrogen-enhanced drug delivery system is applied to the target area of the subject's skin; or wherein delivering the liquid activator is performed after the hydrogen-enhanced drug delivery system is applied to the target area of the subject's skin.

19. The method of claim 10, wherein the subject has a disease, disorder, or condition of the integumentary system, and the method causes a treatment and/or mitigation of the disease, disorder, or condition of the integumentary system.

20. The method of claim 10, wherein the therapeutic agent comprises herbs, herbal-derived compounds, oils, essential oils, Aloe vera, *Hippophae rhamnoides*, sea buckthorn, *Angelica sinensis, Catharanthus roseus, Vinca rosea, Calendula officinalis*, marigold, *Sesamum indicum, Morinda citrifolia*, noni, *Camellia sinensis, Rosmarinus officinalis L.*, rosemary, primrose oil, tea tree oil, propolis, honey, or honey-containing agents.

\* \* \* \* \*